_United States Patent_ [19]

Kramer

[11] 4,426,545

[45] Jan. 17, 1984

[54] ADAMANTYL CARBOXYLIC AND SULFONIC ACID CATALYZED PARAFFIN-OLEFIN ALKYLATION

[75] Inventor: George M. Kramer, Berkeley Heights, N.J.

[73] Assignee: Exxon Research and Engineering Co., Florham Park, N.J.

[21] Appl. No.: 475,450

[22] Filed: Mar. 15, 1983

[51] Int. Cl.$^3$ .......................... C07C 3/12; C07C 3/14; C07C 3/18

[52] U.S. Cl. .................................. 585/724; 585/725; 585/726; 585/727; 585/728; 585/729; 585/730; 585/731; 585/732; 585/721; 585/723

[58] Field of Search ............... 585/724, 725, 726, 728, 585/727, 729, 730, 731, 732

[56] References Cited

U.S. PATENT DOCUMENTS

| | | | |
|---|---|---|---|
| 2,393,152 | 1/1946 | Ellis | 585/731 |
| 3,231,633 | 1/1966 | Kramer | 585/731 |
| 3,382,288 | 5/1968 | Schneider | 585/352 |
| 3,546,308 | 12/1970 | Moore | 585/352 |
| 3,551,514 | 12/1970 | Evering | 585/731 |
| 3,655,807 | 4/1972 | Rakoro et al. | 585/731 |
| 3,671,598 | 6/1972 | Moore | 585/350 |
| 4,162,233 | 7/1979 | Kramer | 585/942 |
| 4,229,611 | 10/1980 | Kramer | 585/728 |
| 4,357,481 | 11/1982 | Kramer | 585/731 |
| 4,357,482 | 11/1982 | Kramer | 585/732 |

OTHER PUBLICATIONS

"Industrial Laboratory Alkylation" edited by Lyle F. Albright and Arthur R. Goldsby, ACS Symposium Series 55, published Washington, D.C., 1977, Chapter One, "Alkylation Studies" by George M. Kramer.

J. Org. Chem. 44, pp. 2619–2624 (1979) by D. Mirda, D. Rapp and G. M. Kramer.

J. Amer. Chem. Soc. 98, pp. 5864–5870 (1976), by P. Van Pelt and H. M. Buck.

Albright et al., "Industrial Laboratory Alkylation," ACS Symposium Series 35, Washington, D.C., (1977) Chap. 1.

Mirda et al., J. Org. Chem., 44, 2619–2624 (1979).

Van Pelt et al., J. Am. Chem. Soc., vol. 98, 5864–5870 (1976).

_Primary Examiner_—Delbert E. Gantz
_Assistant Examiner_—A. Pal
_Attorney, Agent, or Firm_—Robert J. North

[57] ABSTRACT

A process is described for paraffin-olefin alkylation under strong acid conditions in which an adamantylalkyl carboxylic acid or sulfonic acid is used to substantially improve the efficiency of reaction.

25 Claims, No Drawings

ADAMANTYL CARBOXYLIC AND SULFONIC ACID CATALYZED PARAFFIN-OLEFIN ALKYLATION

BACKGROUND OF THE INVENTION

This invention relates to a process for paraffin-olefin alkylation producing highly branched paraffins under strong acid catalyzed conditions and in the presence of adamantyl carboxylic and sulfonic acids as hydride transfer catalysts. The compounds are preferably surfactants in the acid system employed.

The alkylation of olefins with isobutane, which proceeds by the addition of carbonium ions to the olefins under strong acid conditions, is a well-known process for producing a wide variety of useful hydrocarbon materials and particularly, gasoline blending components. For example, 2,2,4-trimethylpentane is a common blending component which is used for octane improvement of motor gasoline and it can be produced by alkylating butenes with isobutane in sulfuric acid or liquid HF. An example of such an acid catalyzed reaction process is described in U.S. Pat. No. 3,231,633.

Hydrocarbon conversion processes employing novel Lewis acid systems are disclosed in U.S. Pat. No. 4,229,611 and U.S. Pat. No. 4,162,233, both assigned to Exxon Research and Engineering Company.

U.S. Pat. No. 3,671,598 describes a process for isomerizing saturated cyclic hydrocarbons under strong acid conditions in the presence of an adamantane hydrocarbon. However, no suggestion is made that the process might be effective in paraffin-olefin alkylation nor that other specifically substituted adamantanes, particularly those with carboxy or sulfoxy substituents, might be more effective in increasing the rate of paraffin-olefin alkylation.

U.S. Pat. Nos. 4,357,481; 4,357,484; 4,357,482; and 4,357,483 to George M. Kramer (issued Nov. 2, 1982, and assigned to Exxon Research and Engineering Company) disclose the use of adamantane hydrocarbons in paraffin-olefin alkylation and non-cyclic paraffin isomerization, and the use of amino alkyladamantanes in paraffin-olefin alkylation and non-cyclic paraffin isomerization, respectively, in which rates of reaction are substantially increased as compared to those obtained in the absence of the specifically disclosed adamantane. However, none of the patents disclose or suggest the use of carboxy- or sulfoxy-containing adamantanes as rate enhancing agents in alkylation or isomerization processes.

New methods for producing such alkylated paraffinic hydrocarbons, useful as octane improvement agents, are constantly being searched for in an effort to increase product quality and process efficiency. Improved processing should lower side reactions, leading to less catalyst consumption while increasing product quality (octane number), yield and reaction rate.

SUMMARY OF THE INVENTION

It has been found that the presence of an adamantyl carboxylic or sulfonic acid in a strong acid system containing an alkyl carbonium ion increases the rate of intermolecular hydride transfer between the alkyl carbonium ion and isobutane or other hydride donors in the system. (These ions are typified by the t-butylcarbonium ion, $t\text{-}C_4H_9^+$.) Since intermolecular hydride transfer is generally the rate-determining step in paraffin-olefin alkylation, see "Industrial Laboratory Alkylation", edited by Lyle F. Albright and Arthur R. Goldsby, ACS Symposium Series 55, Published Washington D.C. 1977, Chapter One "Alkylation Studies" by G. M. Kramer) involving hydride transfer from a paraffin to an alkyl or paraffinic carbonium ion, the presence of the adamantyl acid will serve to increase the reaction rate of the alkylation process. In the production of octane-increasing agents, this should lead to the formation of more selective products having higher octane numbers, lower acid consumption during the process (which is an important economical and environmental consideration) and afford higher yields, which factors enhance the economics of the process.

More specifically, by this invention, there is provided an alkylation process comprising the step of contacting a $C_4$–$C_6$ paraffinic compound, capable of forming a carbonium ion under strong acid conditions, with a $C_2$–$C_5$ olefin in the presence of a strong acid system and an adamantyl carboxylic acid or sulfonic acid, or mixture thereof, said adamantyl compound containing at least one unsubstituted bridgehead position, and said process being conducted at a temperature of about $-100°$ C. to $150°$ C., thereby producing a $C_6$–$C_{11}$ branched paraffinic hydrocarbon.

DESCRIPTION OF THE INVENTION AND PREFERRED EMBODIMENTS

The reason that an adamantane carboxylic acid or adamantane sulfonic acid serves to increase the rate of intermolecular hydride transfer during paraffin-olefin alkylation is not totally understood. One theory that we do not wish to be bound by is that reversible hydride transfer from the bridgehead position of the adamantyl group to a carbonium ion in solution is enhanced due to lack of steric repulsions in the transition state involving the adamantyl group, as compared to hydride transfer involving a paraffinic hydrocarbon and the same carbonium ion.

In the process, $C_3$–$C_5$ olefins can be alkylated with $C_4$–$C_6$ paraffinic compounds to produce effective gasoline octane improvement reagents. Preferably, the starting paraffinic compound is branched such as isobutane, which is capable of forming a tertiary carbonium ion under acid conditions. Normal paraffins can be used instead of branched paraffins when the reaction conditions employ a very strong acid medium capable of catalyzing their isomerization to tertiary carbonium ions (except for propane, which forms the secondary isopropyl cations under very strong acid conditions). Representative examples include isobutane, isopentane, 2-methylpentane, 3-methylpentane, 2,3-dimethylpentane, and mixtures thereof. A preferred paraffin in the process is isobutane and preferred is where isobutane is reacted with $C_3$–$C_5$ olefins to produce $C_7$–$C_9$ branched paraffinic hydrocarbons. Ethylene can also be alkylated, but generally, only with acids which are capable of isomerizing normal paraffins to isoparaffins, e.g., $AlBr_3$.

In the process, carbonium ions can be generated in various ways; in situ from their respective halides, by protonation of an olefin, by oxidation of a paraffin by the acid system, or from a hydrocarbon undergoing an intermolecular hydride transfer reaction with a carbonium ion already present in the acid. The preferred method depends on the acid system, but with $H_2SO_4$ or HF, they are formed readily by protonation of olefins.

Linear or branched $C_2$-$C_5$ olefins or cyclic olefins useful in the process include ethylene, propylene, butene-1, butene-2, isobutylene, cyclopentene, pentene-1, pentene-2, methylbutenes, mixtures thereof, and the like. Preferred olefins are butylenes and amylenes, as for example, feeds available from commercial catalytic cracking streams. Particularly preferred are the butylenes.

The weight ratio of paraffin to olefin used in the process generally varies from about 3 to 1 to 20 to 1, and preferably is about 10 to 1. The olefin space velocity is in the range of about 0.01 to 1 liquid volume olefin/liquid volume of acid/hour. A preferred process is where the olefin and paraffin are introduced into the strong acid system as a feedstream mixture.

The product hydrocarbons in the reaction of isobutane with butylenes are alkylates containing mainly $C_8$ branched paraffins. Representative examples include 2,2,4-, 2,3,4-, 2,3,3-, and 2,2,3-trimethylpentanes, 2,4-, 2,3-, and 2,5-dimethylhexanes, and the like. Preferred products in the process are the trimethylpentanes, which are the main products from the alkylation of butylenes.

Product hydrocarbons in the alkylate, from the alkylation of isobutane and propylene, are mainly a mixture of dimethylpentanes, and from the alkylation of a mixture of amylenes with isobutane, are a mixture of $C_8$ and $C_9$ branched paraffinic hydrocarbons.

The products are useful as gasoline blending agents for octane improvement and/or hydrocarbon solvents.

The phrase "a strong acid system", as used herein, refers to an acid system capable of assisting in generating carbonium ions in the process and includes an "acid component" and a solvent, or a material that can function in both capacities, such as concentrated sulfuric acid preferably being of initial acid strength of about 94 to 99.5 weight percent or liquid HF. The acid system can be solid/liquid, liquid or gaseous. Preferably the acid system is a liquid and particularly preferred is concentrated sulfuric acid having an initial acid strength of about 98 weight percent.

The strong acid components in the acid system are conventional protic and aprotic or Lewis acids and include $AlBr_3$, $AlCl_3$, $GaCl_3$, $TaF_5$, $AsF_5$, $BF_3$, $HF$, $HCl$, $HBr$, $H_2SO_4$, $HSO_3F$, $CF_3SO_3H$, and the like, and mixtures thereof. Preferred acid components in the process are $H_2SO_4$, $HF$, $CF_3SO_3H$, or $HSO_3F$. It should be noted that HCl and HBr are preferably not used alone but are used in combination with other Lewis acids, e.g., $AlCl_3$ and $AlBr_3$. Also noted is that in commercial operations, sulfuric acid strengths lower than 91% by titration, are generally not considered useful.

Also, an ingredient in the "acid system" may be a solvent, required when the acid component is solid, e.g. $AlBr_3$. For Lewis acids, halogenated paraffins and polyhalogenated aromatics are generally used; representative examples include, but are not limited to, $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, $H_2SO_4$, $HSO_3F$, $CF_3SO_3H$, and the like, and mixtures thereof.

The molar concentration of the Lewis acid in these solvents generally varies from 0.1 M to 5.0 M and preferably, the range is between 0.5 M and 2.0 M, based on solvent volume.

The volume ratio of the acid system to the paraffinic hydrocarbon is generally between 5:1 and 1:5 and preferably from 3:1 to 1:3. However, larger and smaller ratios can also be effectively used.

Alkylation reactions are normally carried out in two-phase systems, i.e., an acid phase containing the adamantyl acid, and a hydrocarbon phase. However, alkylation processes can also be carried out in partially miscible media which can be formed, for example, from alkanes, $AlBr_3$ and 1,2,3,4-tetrachlorobenzene.

The adamantyl acid useful in the process contains at least one carboxy or sulfoxy group, preferably being an alkylcarboxy or alkylsulfoxy group, and at least one unsubstituted adamantyl bridgehead position, is preferably surface active, and can be prepared by conventional methods in the art. By the term "surface active", is meant that the adamantyl acid depresses the surface tension of the acid system, and promotes the formation of an emulsion between the acid phase and hydrocarbon phase when used at low concentration, typically in the range of $10^{-6}$ to $10^{-1}$ moles/liter, based on the liquid acid layer.

The adamantyl acid is preferably of the formula:

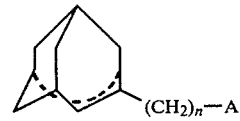

where $n=0-16$, preferably 1-12, most preferably 4-8, $A=COOH$ or $SO_3H$, and wherein the adamantane ring and the alkyl chain can be further modified and substituted with groups which are inert under the process conditions and include $C_1$-$C_4$ alkyl groups, $NO_2$ and $CF_3$ or $C_nF_{2n+1}$ (where $n=1-10$) replacements for the remaining protons provided that at least one adamantyl bridgehead hydrogen remains to promote intermolecular hydride transfer.

Further included are adamantyl compounds in which 2 or 3 of the 4 bridgehead protons of the adamantyl ring are replaced by a $(CH_2)_n$-COOH or $(CH_2)_n$-$SO_3H$ chain, n varying from 0 to 16.

The alkyl chains can also contain non-reactive branches, e.g., $—(CH_2)_n$-C-$(CH_3)_2$-$(CH_2)_m$-A, where $n=(0-10)$, $m=(0-10)$ and A is $—CO_2H$ or $—SO_3H$, wherein the total carbon chain is no more than 16 carbon atoms in length. The neopentyl structure existing in the above illustrated chain is non-reactive in all but the strongest acids and thus, can be used in concentrated $H_2SO_4$ or HF solutions. Expressly excluded is a single methyl group substitution, or its equivalent, which can form reactive tertiary carbonium ions in the process.

Representative examples include 16-(1'-adamantyl)-hexadecanoic acid, 12-(1'-adamantyl)dodecanoic acid, 4-(1'-adamantyl)butanoic acid, 3-(1'-adamantyl)-propanoic acid, 2-(1'-adamantyl)ethanoic acid, 1'-adamantane carboxylic acid, 10-(1'-adamantyl decanoic acid, 8-(1-adamantyl)octanoic acid, 6-(1'-adamantyl)-hexanoic acid, 6-(2'-adamantyl)hexanoic acid, 5-(1'-adamantyl)-2-methylpentanoic acid, 5-(1'-adamantyl)-pentanoic acid, 6-(1'-adamantyl)hexylsulfonic acid, 5-(1'-adamantyl)pentylsulfonic acid, 4-(1'-adamantyl)-butylsulfonic acid, 4-(2'-adamantyl)butylsulfonic acid, 12-(1'-adamantyl)dodecanoic acid, and the like. A preferred catalyst compound is 6-(1'-adamantyl)hexanoic acid. It should also be noted that readily solvolyzed derivatives of these acids and their equivalents such as their esters, anhydrides, acylhalides and amides, which generate the corresponding free acid through solvolysis under "protic acid" reaction conditions, can generally be used in place of the parent adamantyl compounds and are included within the scope of the claimed subject process.

The molar concentration of adamantyl acid in the acid solution varies from about $10^{-6}$ to $10^{-1}$ moles/liter, and preferably about $10^{-4}$ to $10^{-2}$ moles/liter. However, larger and smaller ratios can also be used effectively.

Temperatures in the process are conducted in the range of about $-100°$ to $150°$ C. and preferably about $-50°$ to $100°$ C., depending primarily on the temperature required to obtain a liquid-phase catalyst. A particularly preferred temperature range in concentrated sulfuric acid is $-10°$ C. to $30°$ C.

The process is normally carried out at atmospheric pressure but may also be conducted at higher pressures up to about 20 atmospheres, the pressure depending primarily on the partial pressure of isobutane in the reaction mixture.

Yields of paraffinic branched hydrocarbons in the process range from about 80 to 100 percent of theory, based on starting olefin. Theoretical yield is calculated from the equation:

$$\text{Theo. Yield} = \frac{\text{gms. alkylate produced}}{\text{gms. olefin fed}} \times 100$$

Theoretical yield in the process, on this basis, is 204 %.

Particularly preferred embodiments of the process are where butene-1, butene-2, or isobutylene is reacted with isobutane to produce predominantly a mixture of 2,2,4-, 2,3,4-, 2,3,3- and 2,2,3-trimethylpentanes; where propylene is reacted with isobutane to produce a $C_7$ product comprising 2,3- and 2,4-dimethylpentanes; where isobutane is reacted with a mixture of butenes, as obtained from a petroleum commercial cracking feedstream, to produce a mixture comprising branched $C_8$ paraffinic hydrocarbons, of which about 80 percent can be trimethylpentanes; and where isobutane is reacted with a mixture of amylenes, as obtained from a petroleum commercial cracking feedstream, to produce a mixture comprising predominantly branched $C_8$ and branched $C_9$ paraffinic hydrocarbons.

Apparatus for carrying out the subject process is conventional, either on a laboratory, pilot plant, or full industrial scale and the process can be conducted in a batch-type operation or in a continuous-type operation and in liquid/liquid or liquid/gas systems. The adamantyl acid may also be used in solid/liquid or solid/gas systems, wherein its polar functionality is adsorbed onto or bound by a highly acidic solid acid. A preferred type of process is a liquid/liquid system conducted in a continuous manner.

Generally, the process is conducted by contacting a mixture of paraffin and olefin with a liquid strong acid system mixture containing adamantyl carboxylic acid, adamantyl sulfonic acid, or mixture thereof. If the strong acid system is, for example, concentrated $H_2SO_4$, then the process is conducted in an emulsion of the two-phase system, the acid system usually being the continuous phase although this is not essential to the process. The entire system is preferably at reaction temperature at time of mixing, during which the entire system is vigorously mixed, stirred and agitated to insure good contact between the acid and hydrocarbon phases. The reaction mixture in a commercial reactor is normally transferred to a settler in which the acid and hydrocarbon phases separate on standing. The acid is usually recycled to the reactor after a small portion is drawn-off and replaced with fresh acid. The replacement rate is determined by the extent of acid consumption which can be determined by standard titration procedures.

The hydrocarbon phase is essentially isobutane containing heavier hydrocarbons, which is the alkylation product. This is normally distilled to afford isobutane which is recycled to the reactor, a gasoline boiling range, high octane fraction and heavier fractions which may be used as solvents. The octane number of the gasoline boiling range fraction or "alkylate" can be determined by standard procedures including gas chromatographic analysis.

It is to be understood that obvious modifications and variations on the above-described procedure and subject process, not specifically described herein, are deemed to be encompassed within the general scope and spirit of the application.

The following example is illustrative of the best mode of carrying out the invention, as contemplated by me, and should not be construed as being a limitation on the scope or spirit of the instant invention.

EXAMPLE

This example illustrates the effect of 6-(1'-adamantyl)-hexanoic acid as a catalyst additive on the alkylation of 1-butene with isobutane. The runs were conducted by passing a continuous liquid mixture stream containing 90 weight percent isobutane and 10 weight percent 1-butene through 10 ml. of 98 percent sulfuric acid in a glass reactor with vigorous agitation. The temperature of the contents in the glass reactor was maintained at 10° C. and the process was conducted at about 40 psig pressure. In both the additive and blank runs, the feed was initially passed through the acid in order to fill the reactor within several minutes. After this time, the feed rate was adjusted and a steady state rate of 1 ml of olefin per hour and 9 ml of isobutane per hour was maintained thereafter. As the liquid hydrocarbon stream contacted the acid, an emulsion was formed between the acid, butene and butane forming a lower phase of about 20 to 30 ml. in volume and an upper phase of isobutane. As the alkylation reaction progressed, the alkylate product which was formed in the emulsified region migrated into the upper isobutane layer from which it exited the glass reactor through a control valve. The volume of the upper layer was about 50 ml. The process was allowed to run for several hundred hours with the product being sampled periodically for gas chromatographic analyses, from which the alkylate selectivity (percent of $C_8$ components in the $C_5$ to first major $C_9$ component), MON (motor octane number, clear), yield and extent of cracking could be deduced. The runs using the adamantyl carboxylic acid were carried out with said adamantyl acid present in the sulfuric acid layer at a concentration of $2 \times 10^{-3}$ M. The control was run in the absence of an adamantyl acid. The results are illustrated below in the Table.

The tabulated data are observations which were made at steady state conditions after an initial induction or conditioning period which lasted about 10 to 20 hours. Such periods are known and commonly observed during alkylation and are believed to relate to the buildup of reaction intermediates to a steady state concentration.

The selectivity data in the Table demonstrate that when the adamantyl additive was present, the activity maintenance of the systems was more than doubled, showing the formation of highly selective products for about 360 hours with the additive vs. 150 hours in the blank experiment. The fall-off in selectivity after these times is an indication of the acid strength decreasing to the point that efficient alkylation is no longer occurring.

The data for the unleaded motor octane number (MON, clear) shows that the octane number was also slightly higher and maintained at the higher level for a longer period of time than in the blank experiment as a consequence of the increased hydride transfer rate.

The yield data, which is approximate and requiring stringent data analysis for significant conclusions, showed that the yield for the additive run was almost at the theoretical value for 550 hours on stream. The yield data for the control contained many unexplained variations but was also close to the theoretical value for only 280 hours in comparison.

The degree of cracking, which is essentially the complement weight percentage of selectivity, was substantially reduced in the additive run. As is seen, the degree of cracking in the control was never below about 7 percent, and remained in the 7 to 10 percent range for 140 hours. By contrast, the additive run exhibited only 4 to 7 percent cracking for 250 hours, before showing a 7 to 10 percent degree of cracking in the next 80 hours. At the end of the listed duration period for both runs, the degree of cracking increased significantly.

It is reasonably believed that the degree of cracking in the additive case can be lowered even further by changing the startup procedure such that isobutane alone is fed into the system to fill the volume of the glass reactor up to the control valve under the conditions described in the Example, prior to the introduction of butene-1 into the system. It is reasonably believed that not only would this suppress the degree of cracking, but would also serve to inhibit acid-catalyzed olefin polymerization which would occur particularly with more active olefins, i.e., isobutylene.

TABLE

| Comparisons | Alkylation of 1-Butene | |
|---|---|---|
| | $H_2SO_4$ Control | Adamantyl Additive $2 \times 10^{-3}$ M |
| Selectivity[a] | | |
| To $C_8$ isomers, % | 90-92 | 90-95 |
| Duration, hrs.[b] | 150 | 360 |
| MON, clear[c] | 94-95.5 | 94-96.5 |
| Duration, hrs. | 180 | 380 |
| Yield[d] | >150 | >150 |
| Duration, hrs. | 280 | 550 |
| Cracking[e] | | |
| Range, %, Duration, hrs. | | |
| 4-7 | 0 | 250 |
| 7-10 | 140 | 80 |

[a]Taken as the weight percent of $C_8$ isomers in the product fraction comprising isopentane through 2,4,4-trimethylhexane and included compounds as measured on a gas chromatograph with a Supelco, SP 2110 column.
[b]Duration of run during which the selectivity was maintained in the stated range prior to significant decrease.
[c]Proprietary calculation from the gas chromatographic data used in approximating the unleaded motor fuel performance at high speed and under severe conditions.
[d]Defined as (gms. alkylate/gms. olefin feed) × 100; theoretical yield is 204 percent.
[e]Taken as the weight percent of hydrocarbons in the gas chromatographic fraction, used for determining selectivity, minus $C_8$ isomers.

What is claimed is:

1. An alkylation process comprising the step of contacting a $C_4$-$C_6$ paraffinic compound, capable of forming a carbonium ion under strong acid conditions, with a $C_2$-$C_5$ olefin in the presence of a strong acid system and an adamantyl carboxylic acid, adamantyl sulfonic acid, or mixture thereof, said adamantyl compound containing at least one unsubstituted bridgehead position, and said process being conducted at a temperature of about $-100°$ to $150°$ C., thereby producing a $C_6$-$C_{11}$ branched paraffinic hydrocarbon.

2. The process of claim 1 wherein said paraffinic compound is selected from n-butane, isobutane, n-pentane, isopentane, 2-methylpentane, 3-methylpentane, 2,3-dimethylbutane, isomers thereof, and mixtures thereof.

3. The process of claim 1 wherein said olefin is selected from ethylene, propylene, butene-1, butene-2, isobutylene, linear and branched pentenes, and mixtures thereof.

4. The process of claim 1 wherein said acid system contains an acid component selected from $AlBr_3$, $AlCl_3$, $GaCl_3$, $TaF_5$, $SbF_5$, $AsF_5$, $BF_3$, HF, HBr, HCl, $H_2SO_4$, $HSO_3F$, $CF_3SO_3H$, and mixtures thereof.

5. The process of claim 4 wherein said acid system further contains a solvent selected from $CH_3Br$, $CH_2Br_2$, $CH_2Cl_2$, 1,2-dichloroethane, 1,2,3-trichlorobenzene, 1,2,3,4-tetrachlorobenzene, pentafluorobenzene, HF, concentrated $H_2SO_4$, $HSO_3F$, $CF_3SO_3H$, and mixtures thereof.

6. The process of claim 4 wherein said acid component is HF, concentrated $H_2SO_4$, $HSO_3F$, or $CF_3SO_3H$.

7. The process of claim 1 wherein said adamantyl carboxylic acid or adamantyl sulfonic acid is of the formula:

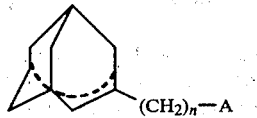

where n=0-16, A=COOH or $SO_3H$ and wherein the adamantyl ring and alkyl chain can be substituted with substituents which are inert or unreactive under the process conditions.

8. The process of claim 7 wherein A in said formula is COOH.

9. The process of claim 8 wherein said adamantyl carboxylic acid is 4-(1'-adamantyl)butanoic acid, 5-(1'-adamantyl)pentanoic acid, or 6-(1'-adamantyl)hexanoic acid.

10. The process of claim 9 wherein said adamantyl carboxylic acid is 6-(1'-adamantyl)hexanoic acid.

11. The process of claim 1 wherein said adamantyl acid is present in a concentration of about $10^{-6}$ to $10^{-1}$ moles per liter based on the amount of said strong acid system.

12. The process of claim 1 wherein said temperature is in the range of about $-50°$ C. to $100°$ C.

13. The process of claim 1 wherein said paraffinic compound and said olefin are contacted as a feedstream mixture with said strong acid system in a respective paraffin/olefin weight ratio of about 3:1 to 20:1.

14. The process of claim 13 wherein said olefin in said feedstream mixture is at a space velocity of about 0.01 to 1 liquid volume olefin/liquid volume acid/hour.

15. The process of claim 1 being conducted in a continuous manner.

16. The process of claim 1 wherein said strong acid system is initially 94 to 99.5 weight percent concentrated sulfuric acid, said adamantyl compound is 6-(1'- adamantyl)hexanoic acid, and said olefin is a $C_3$–$C_5$ olefin.

17. The process of claim 16 wherein said paraffinic compound is isobutane, said olefin is propylene and said product comprises a mixture of dimethylpentanes.

18. The process of claim 16 wherein said paraffinic compound is isobutane, said olefin is a mixture of butenes and said product is an alkylate, comprising branched $C_8$ paraffinic hydrocarbons.

19. The process of claim 16 wherein said paraffinic compound is isobutane, said olefin is a mixture of amylenes, and said product comprises a mixture of branched $C_8$ and $C_9$ paraffinic hydrocarbons.

20. An alkylation process comprising contacting a feedstream of isobutane and a $C_3$–$C_5$ olefin at a paraffin-/olefin weight ratio of 3:1 to 20:1 with concentrated sulfuric acid of 94 to 99.5 weight percent initial acid strength containing 6-(1'-adamantyl)-hexanoic acid, said adamantyl acid present in a concentration of about $10^{-6}$ to $10^{-1}$ moles/liter based on said sulfuric acid, said contacting conducted at an olefin space velocity of about 0.01 to 1 v/v/hr., at a temperature ranging from $-10°$ to $30°$ C. thereby producing an alkylate containing mainly $C_7$–$C_9$ branched paraffinic hydrocarbons.

21. The process of claim 20 wherein said olefin is butene-1, thereby producing an alkylate containing mainly trimethylpentanes.

22. The process of claim 20 wherein said olefin is propylene, thereby producing an alkylate containing mainly dimethylpentanes.

23. The process of claim 20 wherein said olefin is butene-2, thereby producing an alkylate containing mainly trimethylpentanes.

24. The process of claim 20 wherein said olefin is isobutylene, thereby producing an alkylate containing $C_8$ branched paraffinic hydrocarbons.

25. The process of claim 20 wherein said olefin is a mixture of amylenes, thereby producing a mixture of $C_9$ branched paraffinic hydrocarbons.

* * * * *